United States Patent [19]

Layden et al.

[11] 4,143,543

[45] Mar. 13, 1979

[54] MECHANICAL ACCELERATION MULTIPLIER FOR MICROCIRCUIT BOND TESTING

[75] Inventors: Owen P. Layden; Francis J. Murdoch, both of Monmouth Beach, N.J.

[73] Assignee: The United States of America as represented by the Secretary of the Army, Washington, D.C.

[21] Appl. No.: 849,735

[22] Filed: Nov. 9, 1977

[51] Int. Cl.$^2$ ............................................. G01N 19/04
[52] U.S. Cl. ..................................... 73/827; 73/150 A
[58] Field of Search ................ 73/88 B, 150 A, 150 R

[56] References Cited

U.S. PATENT DOCUMENTS 3,290,929  12/1966  Sheldon ................................. 73/95

FOREIGN PATENT DOCUMENTS 2357268  5/1975  Fed. Rep. of Germany ........... 73/88 B

OTHER PUBLICATIONS

"Adhesion Measurement of Thin Films", from "Electrocomponent Science and Technology" vol. 3, No. 1, pp. 21-42, 6-76 pp. 27-29.
"Spin Test Solder Reflow Joints", IBM Technical Disclosure Bulletin vol. 17, No. 3, p. 657, 8-1974.
"Determining the Adhesion Strength . . ." from Industrial Laboratory vol. 40, No. 1, 134-136, 1-1974.

Primary Examiner—James J. Gill
Attorney, Agent, or Firm—Nathan Edelberg; Sheldon Kanars; Edward Goldberg

[57] ABSTRACT

A mechanical acceleration multiplier for testing the bond strength of an adhesive wherein the adhesive to be tested is subjected to a centrifugal force.

5 Claims, 3 Drawing Figures

MECHANICAL ACCELERATION MULTIPLIER FOR MICROCIRCUIT BOND TESTING

The invention described herein may be manufactured and used by or for the Government for governmental purposes without the payment of any royalties thereon or therefor.

BACKGROUND OF THE INVENTION

When placing electronic circuitry behind enemy lines for surveillance purposes, hybrid microelectronic packages are employed which include small chip components bonded on substrates which are bonded to a package. These packages are placed behind the enemy lines by either "air drop" or "artillery firing" techniques. Whichever technique is employed, the chip and substrate bonds are subjected to high G forces which can cause a circuit failure if the bond cannot withstand the high G or high shock environment. Accordingly, it is desirable to conduct tests on the various adhesives employed in the packages to establish their reliability under high G environments.

Heretofore, the bond strength of organic material and solders have been tested by simple pull tests of the type disclosed in U.S. Pat. Nos. 896,191; 1,991,854; 2,834,205; and 3,336,797 wherein an adhesive is secured between a pair of components to which oppositely acting pulling forces are applied by means of a calibrated pull tester. This technique is unsatisfactory for components subjected to high shock applications since resonances of high G levels may appear for short durations. Furthermore, the pull test technique is difficult to perform when the components are small, as in hybrid micro-circuits, because of the difficulty of making a connection from the pull tester to the component.

After considerable research and experimentation, the bond tester of the present invention has been devised to overcome the disadvantages experienced with conventional pull testers, and comprises, essentially, a rotary arm having the adhesive to be tested interposed between the outer end thereof and the substrate or component to be bonded. Upon rotation of the arm, a force is generated along the face of the adhesive in an outwardly radial direction. By adding additional masses to the component adhered to the outer end of the rotary arm, the pulling effect on the bond can be multiplied to obtain the desired G forces which the component and adhesive will experience in actual use.

DESCRIPTION OF THE PREFERRED EMBODIMENT

Figure 2:
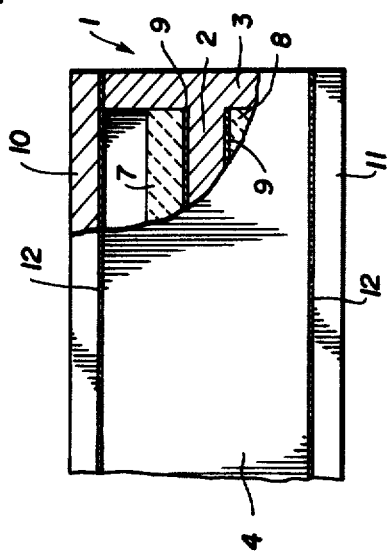
FIG. 2 is a fragmentary, side elevational view, partly in section, of an assembled micro-electronic package.
Figure 1:
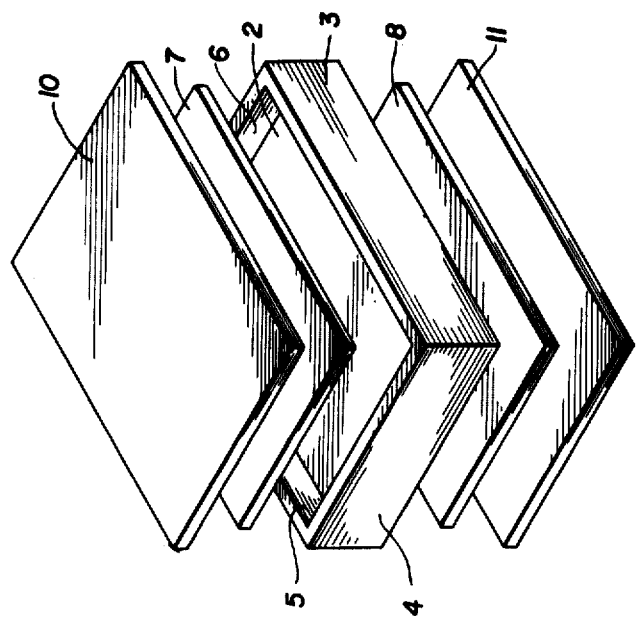
FIG. 1 is an exploded, perspective view of a micro-electronic package.

Referring to the drawings, and more particularly to FIGS. 1 and 2 thereof, a micro-electronic package is shown which includes a housing 1 having an intermediate wall, or common header 2 extending between and connected to the housing side walls 3, 4, 5 and 6. Substrates 7 and 8 containing hybrid micro-electronic circuits are secured to the opposite faces of the header 2 by means of a suitable adhesive 9 such as an expoxy. Closures 10 and 11 are applied to the housing on each side thereof and secured thereto as at 12 by welding, soldering or epoxying.

Due to the high G forces applied to the micro-electronic packages when being placed behind enemy lines, either by air drop or artillery firing, it is important that the epoxy 9 and 12 maintain the various components of the package in the assembled position. To assure that the particular adhesive employed in the package will maintain the bond while experiencing the high G forces, the tester of the present invention has been devised to determine the bond strength of the particular epoxy.

Figure 3:
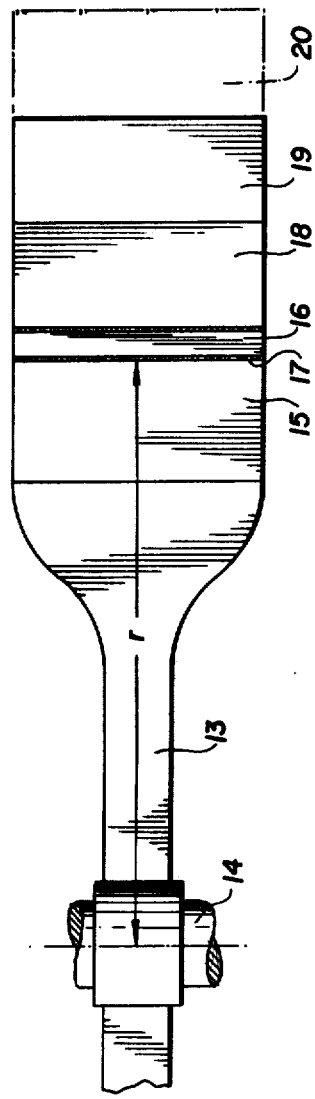
FIG. 3 is a fragmentary, side elevational view of the tester of the present invention employed for testing the bond strength of the adhesive used in the micro-electronic package shown in FIGS. 1 and 2.

As will be seen in FIG. 3, the tester of the present invention comprises an arm 13 connected to a rotary shaft 14 adapted to be driven by a suitable motor (not shown). A carrier plate 15 is provided on the outer end of the arm to which a sample component 16, having a mass m, is bonded by an adhesive to be tested, 17.

When the arm 13 is rotated at a desired velocity, the adhesive 17 is subjected to a pulling force in an outwardly radial direction. The force on the bond is determined by the formula:

$$F = mV^2/r$$

where m is the mass of the component 16,

V is the velocity of rotation of the arm 13, and r is the distance indicated in FIG. 3.

If it is desired to increase the pulling force on the adhesive, additional sample components 18, 19 and 20 having masses $M_1$, $M_2$ and $M_3$, respectively, may be selectively attached to the outer face of the sample component 16. The pulling force on the bond is then determined by the formula:

$$F = (m + M_1 + M_2 \ldots) V^2/r$$

By the construction and arrangement of the mechanical acceleration multiplier of the present invention, G forces of 120,000 can be obtained which are equivalent to the G forces experienced by the adhesive in the package during the placement thereof behind enemy lines.

It is to be understood that the form of the invention herewith shown and described is to be taken as a preferred example of the same and that various changes in the shape, size and arrangement of parts may be resorted to, without departing from the spirit of the invention or scope of the subjoined claims.

We claim:

1. A mechanical acceleration device for testing the bond strength of an adhesive comprising, a shaft rotatable about a central axis, a rotary arm secured to and extending radially from said shaft, an adhesive layer to be tested disposed on the outer peripheral end of said arm and extending parallel to said axis, a component bonded to said outer end of said arm by said adhesive layer and extending parallel to said axis, whereby upon rotation of said arm a pulling force is imparted by said component to said adhesive layer in an outwardly radial direction.

2. The mechanical acceleration device according to claim 1, wherein said component comprises a substrate including a microcircuit.

3. The mechanical acceleration device according to claim 1, wherein additional components are selectively attached to and positioned outwardly from said first mentioned component to thereby increase the pulling force on said adhesive layer during the rotation of said arm.

4. A method of determining the bond strength of an adhesive, comprising the steps of:

securing a radially extending arm having a length r to a shaft rotatable about a central axis;

coating the outer peripheral end of said arm with a film of the adhesive to be tested, said film extending parallel to said axis;

firmly placing a component having a mass "m" on said adhesive film to adhere to said film and extend parallel to said axis; and rotating said arm about said axis at a desired velocity, v, to generate a pulling force, F, against said adhesive film in an outward radial direction, whereby the pulling force, F, on the adhesive is determined by the formula:

$$F = mv^2/r.$$

5. The method determining the bond strength of an adhesive according to claim 4, wherein additional components having masses $M_1, M_2 \ldots$ are selectively attached to and positioned outwardly from said component having a mass, m, to thereby increase the pulling force, F, on the adhesive, whereby the pulling force, F, on the adhesive is determined by the formula:

$$F = (m + M_1 + M_2 \ldots) V^2/r.$$

* * * * *